United States Patent
Murakami (10) Patent No.: US 6,328,703 B1
(45) Date of Patent: Dec. 11, 2001

(54) ULTRASONIC TREATING APPARATUS

(75) Inventor: Eiji Murakami, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/605,254

(22) Filed: Jun. 28, 2000

(30) Foreign Application Priority Data

Jul. 2, 1999 (JP) .................................................. 11-189095

(51) Int. Cl.$^7$ .................................................. A61H 1/00
(52) U.S. Cl. .................................. 601/4; 601/2; 606/41
(58) Field of Search ...................... 601/2–4; 606/1, 606/41; 600/439, 437

(56) References Cited

U.S. PATENT DOCUMENTS

| | | | |
|---|---|---|---|
| 5,322,055 | * | 6/1994 | Davison et al. ......................... 601/2 |
| 6,193,709 | * | 2/2001 | Miyawaki et al. ....................... 606/1 |
| 6,206,844 | * | 3/2001 | Reichel et al. .......................... 601/2 |

FOREIGN PATENT DOCUMENTS 10-5237   1/1998   (JP) .

* cited by examiner

*Primary Examiner*—Justine R. Yu
(74) *Attorney, Agent, or Firm*—Frishauf, Holtz, Goodman, Langer & Chick, P.C.

(57) ABSTRACT

A ultrasonic treatment apparatus of the present invention comprises a ultrasonic vibrator for generating ultrasonic vibration, a vibration transmitting member connected to the ultrasonic vibrator at a proximal end thereof, the vibration transmitting member transmitting ultrasonic vibration generated by the ultrasonic vibrator and having a treatment section for treating tissues of a living body by the transmitted ultrasonic vibration at a tip end thereof, a sheath removably mounted to the ultrasonic vibrator, the sheath covering the substantially entire vibration transmitting member excluding the treatment section from the outside, a high-frequency power connection connector provided at the sheath, the connector electrically connected to a high-frequency power source via a cable for supplying a high-frequency current, and a conductive member for electrically connecting the high-frequency power connection connector to the vibration transmitting member.

8 Claims, 7 Drawing Sheets

ULTRASONIC TREATING APPARATUS

CROSS-REFERENCE TO RELATED APPLICATIONS

This application is based upon and claims the benefit of priority from the prior Japanese Patent Application No. 11-189095, filed Jul. 2, 1999, the entire contents of which are incorporated herein by reference.

BACKGROUND OF THE INVENTION

The present invention relates to a ultrasonic treatment apparatus for treating a living body by utilizing a frictional head caused by ultrasonic vibration. In particular, the present invention relates to a ultrasonic treatment apparatus capable of performing electronic high-frequency treatment by a supplied high-frequency current.

Conventionally, a variety of ultrasonic treatment apparatuses for performing treatment such as tissue dissection or coagulation by utilizing ultrasonic vibration energy have been known. Of such ultrasonic treatment apparatuses, a ultrasonic treatment apparatus capable of performing electronic high-frequency treatment by a supplied high-frequency current is disclosed in Jpn. Pat. Appln. KOKAI Publication No. 10-5237, for example.

The ultrasonic treatment apparatus disclosed in the above specification comprises: a ultrasonic vibrator having an element for converting an electric signal to ultrasonic vibration incorporated therein; a probe removably mounted to this ultrasonic vibrator by screws, the probe serving as a vibration transmitting member for transmitting ultrasonic vibration generated from the ultrasonic vibrator; and a sheath serving as an elongated insert section into which this probe is inserted.

A tip end portion of the probe is protruded from a tip end of the sheath, and is formed as a treatment section for treating tissues by ultrasonic vibration. In addition, a connection pin by which an electric cable connected to a high-frequency power source is mounted is provided at the ultrasonic vibrator. In this case, the high-frequency current from the high-frequency power source is supplied to the probe via the connection pin and an electric circuit provided inside of the ultrasonic vibrator. An insulation tube for insulating a high-frequency current is covered at the outside of the sheath.

On the other hand, some types of ultrasonic treatment apparatuses are designed to treat tissues by ultrasonic vibration while the tissues are grasped. In such type of ultrasonic treatment apparatus, jaws serving as a gripping member are turnably mounted to a tip end of the sheath. In addition, the tip end portion of the probe is extruded from an opening at the tip end of the sheath so as to be opposite to jaws, and is formed as a treatment section for treating tissues gripped between the jaws by ultrasonic vibration.

In addition, the jaws are linked with an operating rod inserted into the sheath. When the operating rod is operated to be pushed or pulled by handle operation at a frontal operating section, the rod is turned between a closed position abutting against the treatment section at the tip end of the probe and an open position spaced from the treatment section at the tip end of the probe.

As described previously, in a conventional ultrasonic treatment apparatus capable of performing electrical high-frequency treatment by a high-frequency current, a connection pin for electrical connection with a high-frequency power source is provided at a ultrasonic vibrator, and an electric circuit for supplying a high-frequency current to a probe is provided inside of the ultrasonic vibrator. This makes the structure of the ultrasonic vibrator complicated, thereby increasing manufacturing cost.

In addition, even in a ultrasonic treatment apparatus which is not compatible with high-frequency treatment, in the case where a high-frequency connection pin is provided at a ultrasonic vibrator, it is required to apply electrical insulation processing to a portion other than a required portion or provide a specific ultrasonic vibrator in which a high frequency cannot be used. In the former case, the treatment apparatus itself becomes expensive. In the latter case, a user must provide two types of ultrasonic vibrators, resulting in higher cost.

BRIEF SUMMARY OF THE INVENTION

It is one object of the present invention to provide an inexpensive ultrasonic treatment apparatus capable of performing electronic high-frequency treatment by a high-frequency current without complicating the structure of a ultrasonic vibrator.

This object of the present invention is achieved by the following ultrasonic treatment apparatus. That is, the ultrasonic treatment apparatus according to the present invention comprises: a ultrasonic vibrator for generating ultrasonic vibration; a vibration transmitting member connected to the ultrasonic vibrator at its proximal end, the vibration transmitting member transmitting ultrasonic vibration generated by the ultrasonic vibrator and having a treatment section for treating tissues of a living body by the transmitted ultrasonic vibration at its tip end; a sheath removably mounted to the ultrasonic vibrator, the sheath covering the substantially entire vibration transmitting member excluding the treatment section from the outside; a high-frequency power connection connector provided at the sheath, the connector being electrically connected to a high-frequency power source via a cable for supplying a high-frequency current; and a conductive member for electrically connecting the high-frequency power connection connector to the vibration transmitting member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Hereinafter, embodiments of the present invention will be described with reference to the accompanying drawings.

Figure 1:
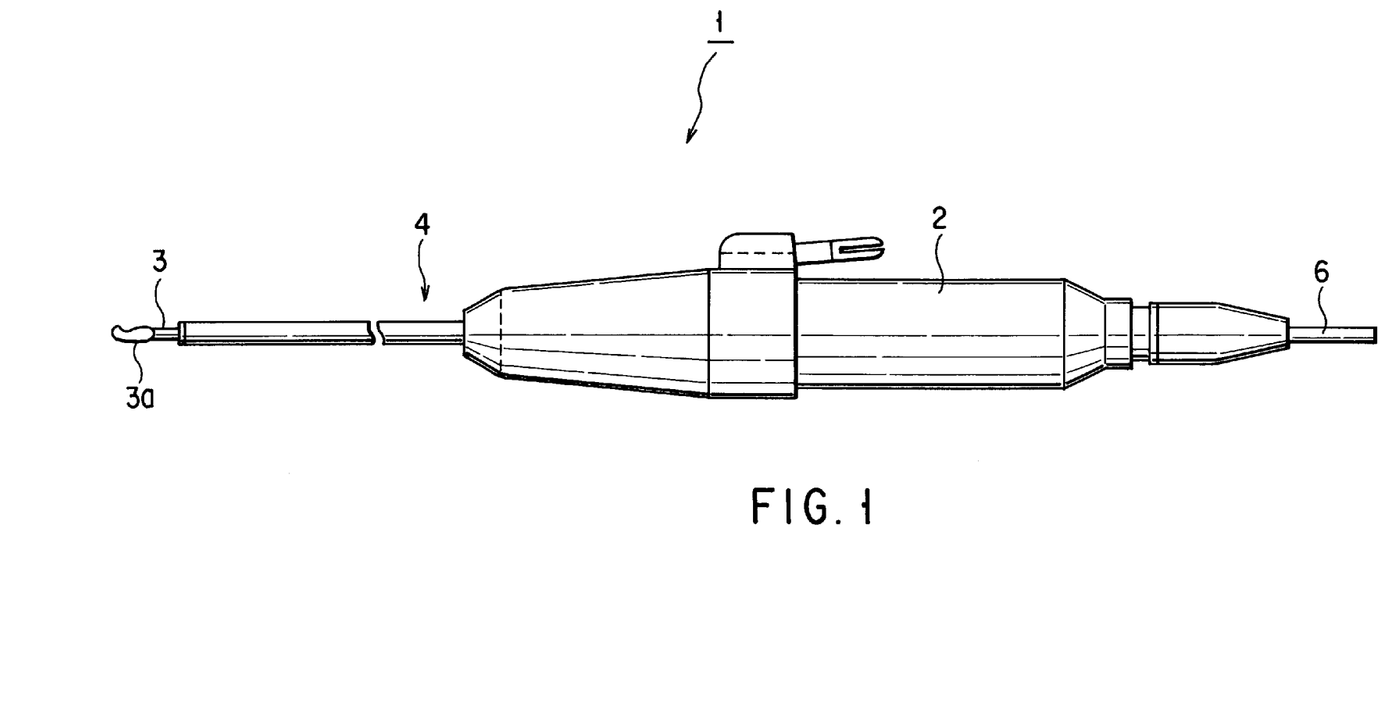
FIG. 1 is a side view showing a ultrasonic treatment apparatus according to a first embodiment of the present invention.
Figure 2:
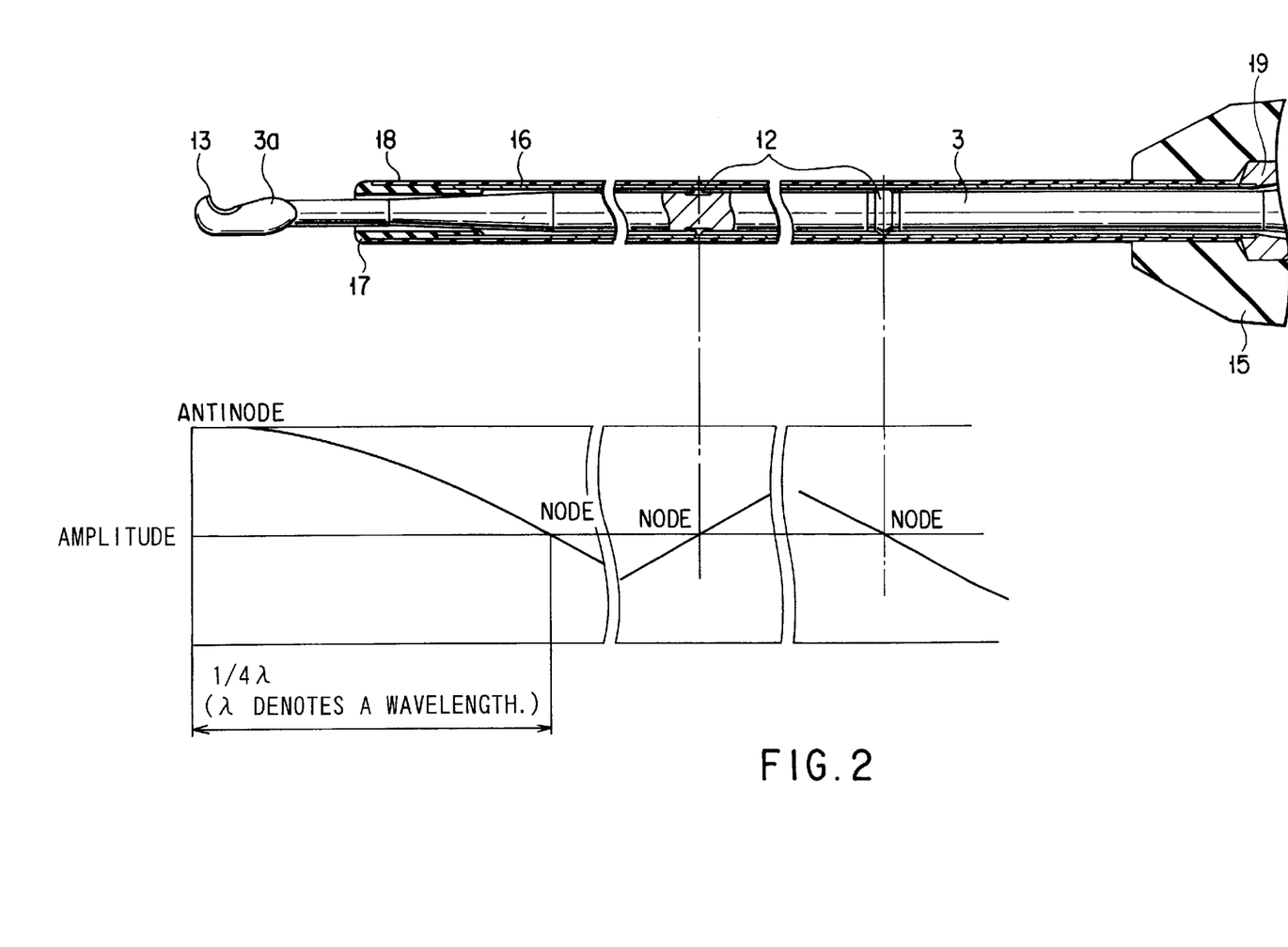
FIG. 2 is a sectional view showing an insert section of the ultrasonic treatment apparatus shown in FIG. 1.
Figure 3:
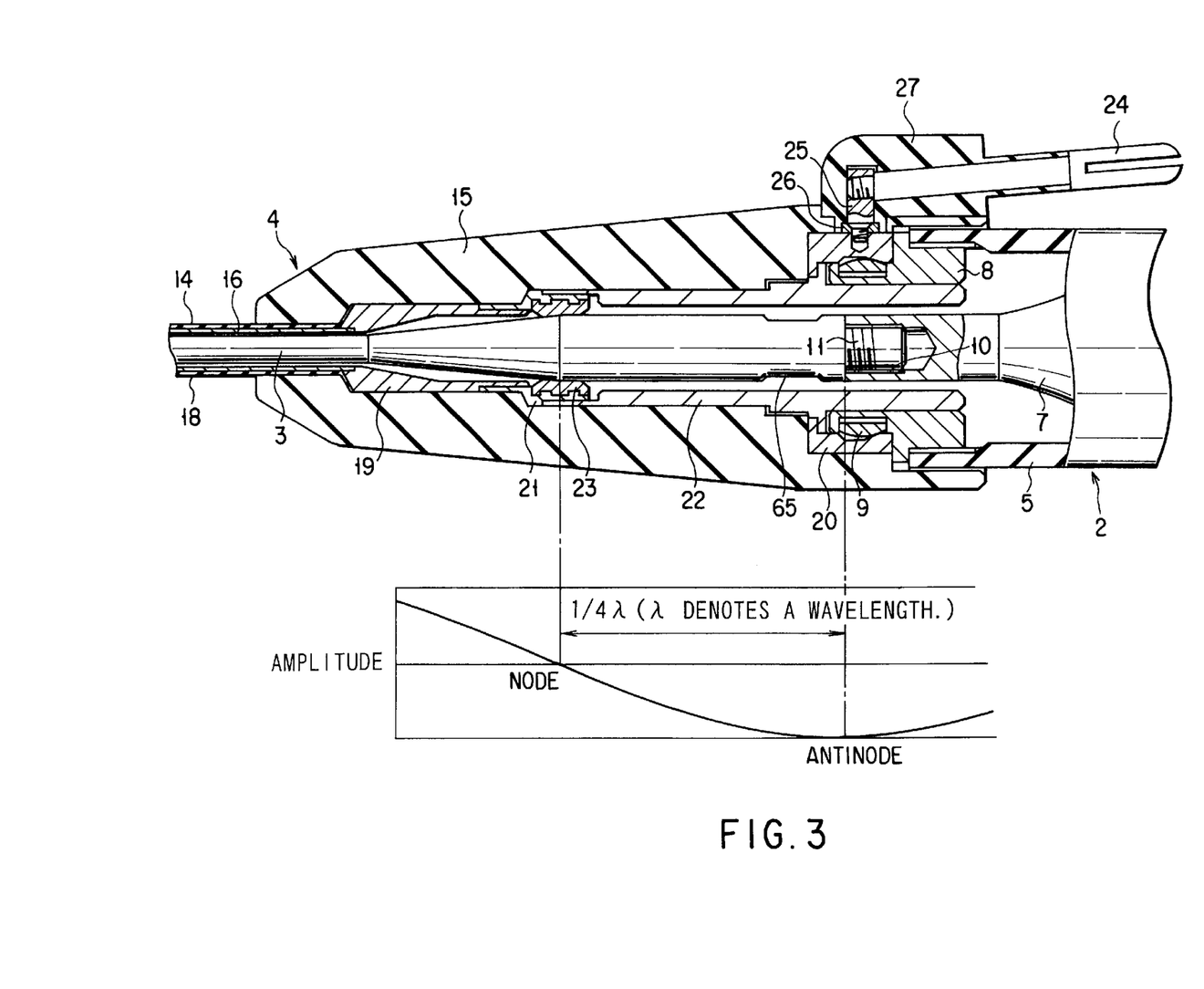
FIG. 3 is a sectional view showing an operating section of the ultrasonic treatment apparatus shown in FIG. 1.

FIGS. 1 to 3 show a first embodiment of the present invention. As shown in FIG. 1, a ultrasonic treatment apparatus 1 according to the present embodiment consists of a ultrasonic vibrator 2 for generating ultrasonic vibration; a probe 3 serving as a vibration transmitting member for transmitting ultrasonic vibration generated by the ultrasonic vibrator 2; and a sheath 4 through which the probe 3 is inserted. In this case, a tip end portion of the probe 3 is protruded from a tip end of the sheath 4, and is formed as a treatment section 3a for treating tissues by ultrasonic vibration.

A piezoelectric element for converting a current to ultrasonic vibration is incorporated into the ultrasonic vibrator 2. In addition, a cable 6 for supplying a current (a current for ultrasonic vibration) from a power source unit (not shown) to the ultrasonic vibrator 2 is extended from a proximal end of the ultrasonic vibrator 2.

As shown in FIG. 3, the ultrasonic vibrator 2 has a vibrator cover 5 for covering the piezoelectric element. To a tip end of the ultrasonic vibrator 2, there are fixed a horn 7 for transmitting ultrasonic vibration while the amplitude of ultrasonic vibration is extended to some extent; and an attachment 8 to which the sheath 4 is connected. A partly cutout metallic ring 9 is mounted to the attachment 8.

A screw section 10 to which the probe 3 is mounted is provided at the tip end of the horn 7. In addition, a screw section 11 which is removably mounted to the screw section 10 of the horn 7 is provided at the proximal end of the probe 3. The probe 3 and the horn 7 are abutted so as to be butted against each other at a position of the antinode of ultrasonic vibration generated from the ultrasonic vibrator 2.

A recess-shaped tool hooking section 65 for hooking a tool to be used for removably connecting the probe 3 to the horn 7 is provided neat the proximal end portion of the probe 3. In addition, the probe 3 is decreased in a sectional area in an axial direction at a nodal position of vibration which is present intermediately of the probe so that an amplitude required for treatment can be obtained at the treatment section 3a by extending the amplitude of ultrasonic vibration. Further, a length of the probe 3 is set to an integer multiple of a half wavelength (½λ) of the ultrasonic wave generated from the ultrasonic vibrator 2 so that the treatment section 3a corresponds to antinode of a vibration.

As shown in FIG. 2, elastomer based rubber rings 12 for supporting the probe 3 in the sheath 4 and preventing interference between the sheath 3 and the probe 3 are mounted to several nodal parts of vibration which is present intermediately of the probe 3. This rubber ring 12 may be fabricated by a conductive elastomer member. In addition, a hook section 13 for performing treatment such as dissection by hooking tissues is provided at the treatment section 3a of the probe 3.

As shown in FIG. 3, the sheath 4 consists of an insert section 14 to be inserted into cavities of the patient's body during surgical operation; and a main body 15 gripped by the surgeon's hand. The main body 15 is formed by an electric insulation member. A metallic pipe 16 is arranged inside of the insert section 14, and a cap 17 consisting of an electric insulation member is fixed to the tip end portion of a pipe 16 (refer to FIG. 2). In addition, at the outside of the pipe 16, an insulation tube 18 is covered from the cap 17 at the tip end side over the main body 15 at the proximal end side.

The proximal end portion of the pipe 16 is fixed to a metallic pipe fixing member 19 arranged inside of the main body 15. In addition, a metallic connecting member 20 having a groove removably engaged with a ring 9 provided on the ultrasonic vibrator 2 side is fixed to the proximal end side of the main body 15. That is, the sheath 4 is removably mounted to the ultrasonic vibrator 2 side. In addition, a connecting member 20 is connected to a pipe fixing member 19 via metallic intermediate members 21 and 22 fixedly disposed in the main body 15.

A rubber member 23 made of a conductive elastomer is fixed to the intermediate member 21. This rubber member 23 is designed to come into contact with the peripheral face of the probe 3 at a nodal position of vibration which is the closest to the proximal end of the probe 3 while the sheath 4 is mounted to the ultrasonic vibrator 2.

A connecting pin 24 serving as a high-frequency power connection connector is mounted and fixed to the connecting member 20 via a pin fixing member 25. A cable for supplying a high-frequency current from a high-frequency power source (not shown) is connected to the connecting pin 24. A rubber ring 26 consisting of a conductive elastomer is sandwiched between the pin fixing member 25 and the connecting member 20 in order to ensure good electrical connection. In addition, a part other than the required parts of the connecting pin 24 and the pin fixing member 25 is covered with an insulation cover 27.

In the ultrasonic treatment apparatus 1 having such configuration, the connecting pin 24 is electrically connected to the probe 3 via each of the members 25, 26, 20, 22, 21, and 23 made of a conductive material. In addition, in the case where the rubber ring 12 provided at a nodal of vibration of the probe 3 is formed by a conductive elastomer, the connecting pin 24 is electrically connected to the probe 3 even via each of the members 25, 26, 20, 22, 21, 19, 16, and 12 made of a conductive material.

As has been described above, in the ultrasonic treatment apparatus according to the present embodiment, a high-frequency connecting pin 24 is provided at the sheath 4 through which the probe 3 is inserted. This pin 24 is electrically connected to the probe 3 at a nodal position of ultrasonic vibration transmitted by the probe 3 by means of a metal member or conductive elastomer member provided inside of the sheath 4. Therefore, electrical high-frequency treatment using a high-frequency current can be performed without providing the connecting pin for electrical connection to the high-frequency power source at the ultrasonic vibrator, and providing an electric circuit for supplying a high-frequency current to the probe inside of the ultrasonic vibrator. That is, electronic high-frequency treatment using a high-frequency current can be performed inexpensively without complicating the structure of the ultrasonic vibrator (the structure of the ultrasonic vibrator can be simplified more significantly than a conventional vibrator). In addition, with respect to application in which a high-frequency device is not used because of probe type, a high-frequency power connecting cable is not mounted to the ultrasonic vibrator. Therefore, there is provided an advantage that, even if insulation is not applied to an insert section or the like, high-frequency power supply due to misuse can be avoided. Further, there is provided an advantage that the ultrasonic vibrator becomes inexpensive because there is no need to apply unnecessary insulation to the application side.

Figure 4:
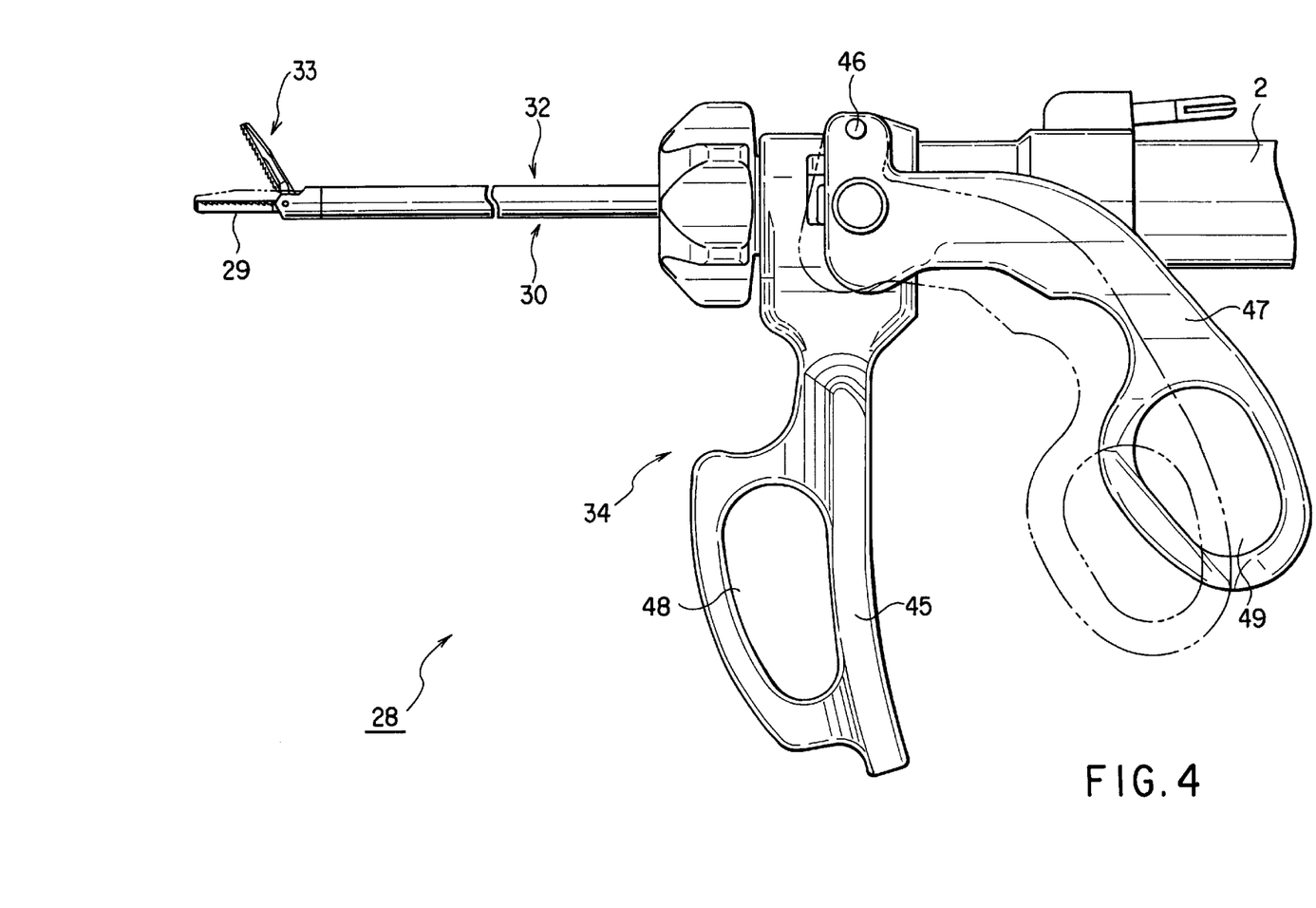
FIG. 4 is a side view showing a ultrasonic treatment apparatus according to a second embodiment of the present invention.

FIGS. 4 to 9 show a second embodiment of the present invention. As shown in FIG. 4, a ultrasonic treatment apparatus 28 according to the present embodiment comprises three units: a ultrasonic vibrator 2; a probe 29 serving as a vibration transmitting member; and a sheath 30. The tip end portion of the probe 29 is protruded from the tip end of the sheath 30, and is formed as a treatment section 29a for treating tissues by ultrasonic vibration. In addition, the configuration of the ultrasonic vibration 2 is identical that of the first embodiment. Like elements are represented by like reference numerals, and a description of the vibrator will be omitted here.

Figure 7:
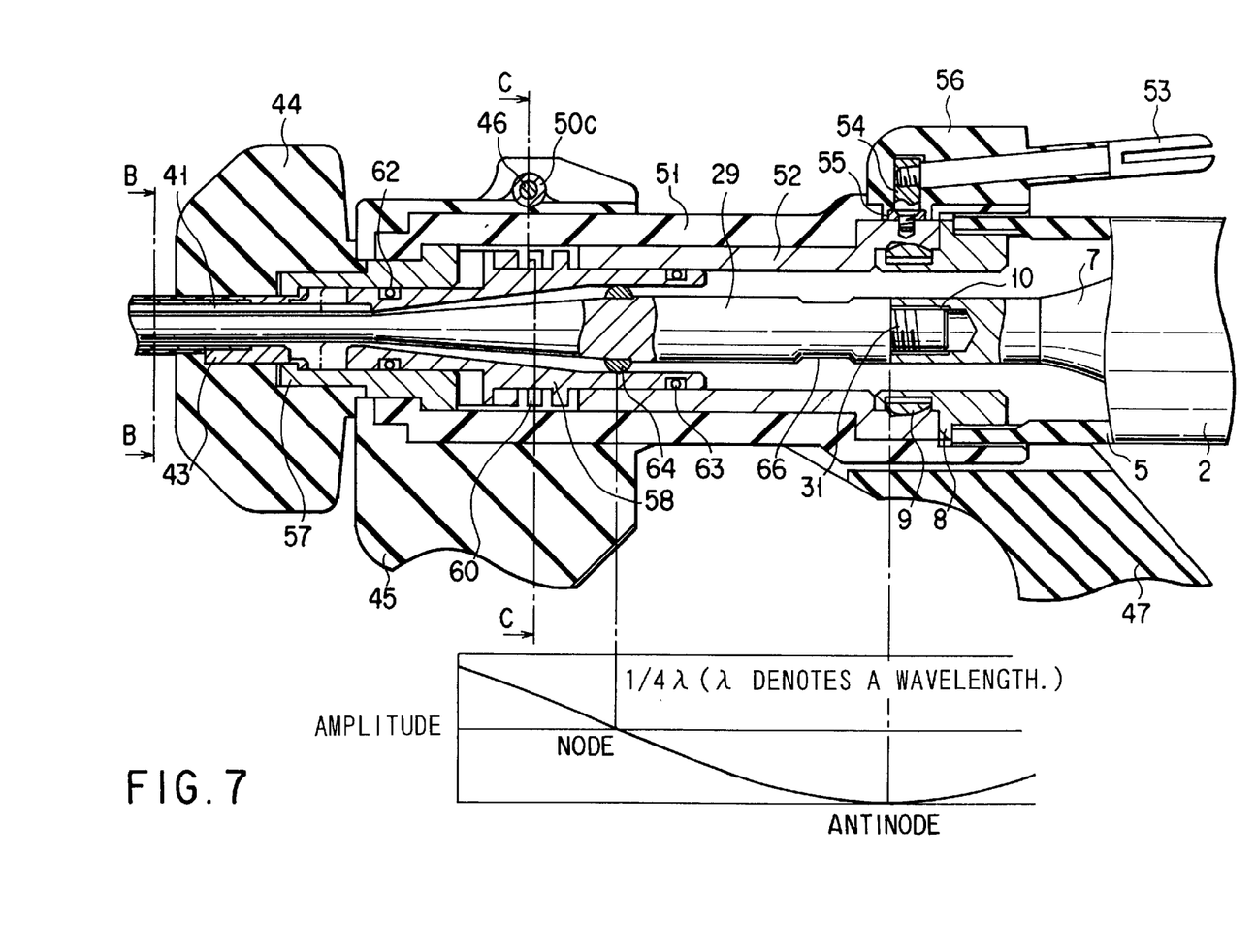
FIG. 7 is a sectional view showing an operating section of the ultrasonic treatment apparatus shown in FIG. 5.

As shown in FIG. 7, a screw section 31 removably connected to a screw section 10 provided at a horn 7 is provided at the proximal end portion of the probe 29. In addition, a length of the probe 29 is set to an integer multiple of a half wavelength (½λ) of the ultrasonic wave generated from the ultrasonic vibrator 2. Further, a conductive rubber ring 64 is mounted to the proximal end portion of the probe 29. This rubber ring 64 is fixed to the peripheral face of the probe 3 at a nodal position of vibration which is the closest to the proximal end of the probe 29.

Figure 5:
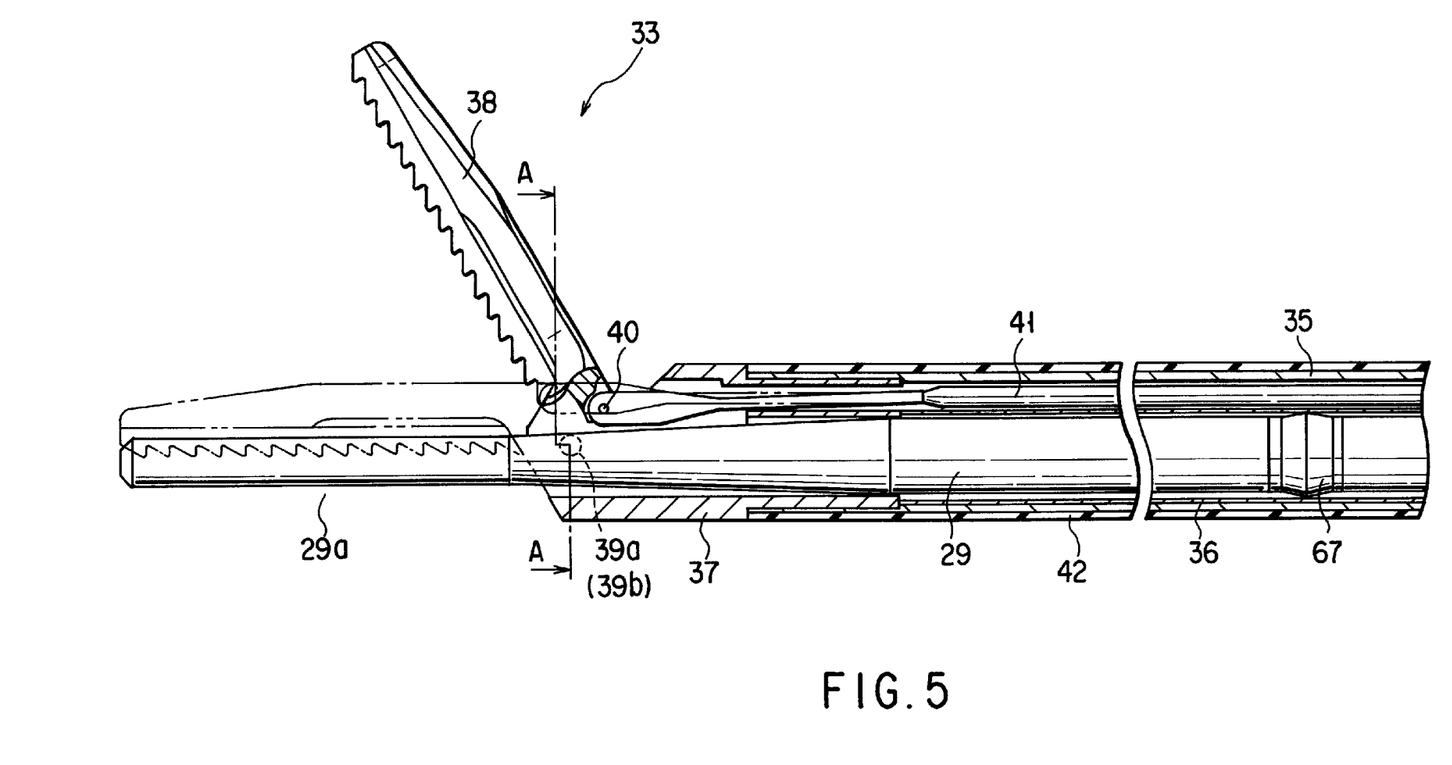
FIG. 5 is a sectional view showing a tip end of an insert section of the ultrasonic treatment apparatus shown in FIG. 4.

As shown in FIG. 5, elastomer based rubber rings 67 for supporting the probe 29 in the sheath 30 and preventing interference between the sheath 30 and the probe 29 are mounted at several nodal portions of vibration which is present intermediately of the probe 29. This rubber ring 67 may be fabricated by a conductive elastomer member.

A recess-shaped tool hooking section 66 for hooking a tool to be used for removably mounting a probe 29 is provided near the proximal end portion of the probe 29 to the horn 7 (refer to FIG. 7). In addition, a treatment section 29e at the tip end of the probe 29 is formed in a round bar shape (refer to FIG. 4 and FIG. 5).

As shown in FIG. 4, a sheath 30 consists of an insert section 32 to be inserted into cavities of the patient's body during surgical operation; and an operating section 34 for operating a tip end serving section 33 provided at the tip end of the sheath 30.

Figure 8:
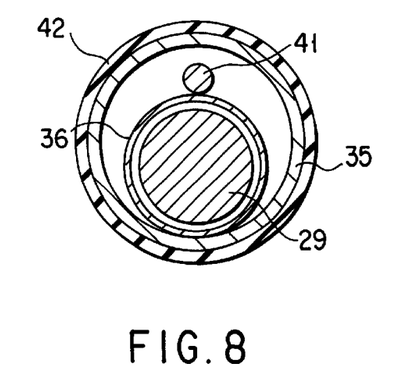
FIG. 8 is a sectional view taken along the line B—B shown in FIG. 7.

As shown in FIG. 5 and FIG. 8, an insert section 32 consists of an outer pipe 35; and an inner pipe 36 arranged inside of the outer pipe, the inner pipe 36 through which the probe 29 is inserted. The tip end portion of each of the pipes 35 and 36 is fixed by a tip end cover 37. In addition, the inner diameter of the inner pipe 36 is set to be smaller than the outer diameter of a rubber ring 67 so that the rubber ring 67 comes into close contact with the inner pipe 36 over its entire periphery. In addition, at the outer periphery of the outer pipe 35, an insulation tube 42 is covered from the tip end cover 37 over the proximal end portion of the outer pipe 35. As shown in FIG. 7, at the proximal ends of the outer pipe 35 and the inner pipe 36, a rotating knob 44 consisting of an insulation member is mounted via a pipe fixing member 43.

Figure 6:
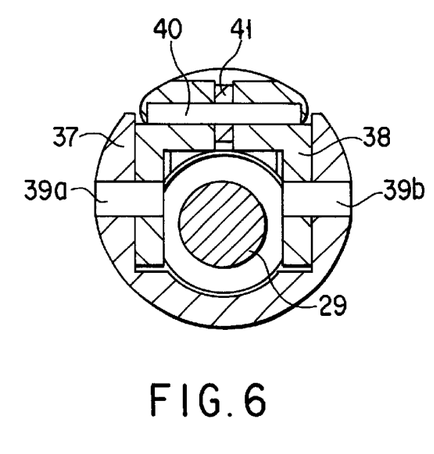
FIG. 6 is a sectional view taken along the line A—A shown in FIG. 5.

As shown in FIG. 5 and FIG. 6, jaws 38 for gripping tissues between the treatment sections 39a at the tip end of the probe 29 are turnably fixed to the tip end cover 37 via fulcrum pins 39a and 39b. A driving shaft 41 is fixed to the proximal end of the jaws 38 via the pin 40. This driving shaft 41 passes through between the outer pipe 35 and the inner pipe 36, and extends to the operating section 34. This driving shaft 41 is advanced or retracted in the axial direction, whereby the jaws 38 are turned about fulcrum pins 39a and 39b between a closed position meshed with the treatment section 29a of the probe 29 (a position indicated by two-dots-chain line shown in FIG. 5) and an open position spaced from the treatment section 29a (a position indicated by solid line shown in FIG. 5).

As shown in FIG. 4, an operating section 34 comprises; a fixing handle 45 removably mounted to the ultrasonic vibrator 2; and a movable handle 47 turnably mounted to the fixing handle 45 via the fulcrum pin 46. Finger hook sections 48 and 49 are formed at the fixing handle 45 and the movable handle 47, respectively. By hooking and gripping these sections, the movable handle 47 can be turned via the fulcrum pin 46.

Figure 9:
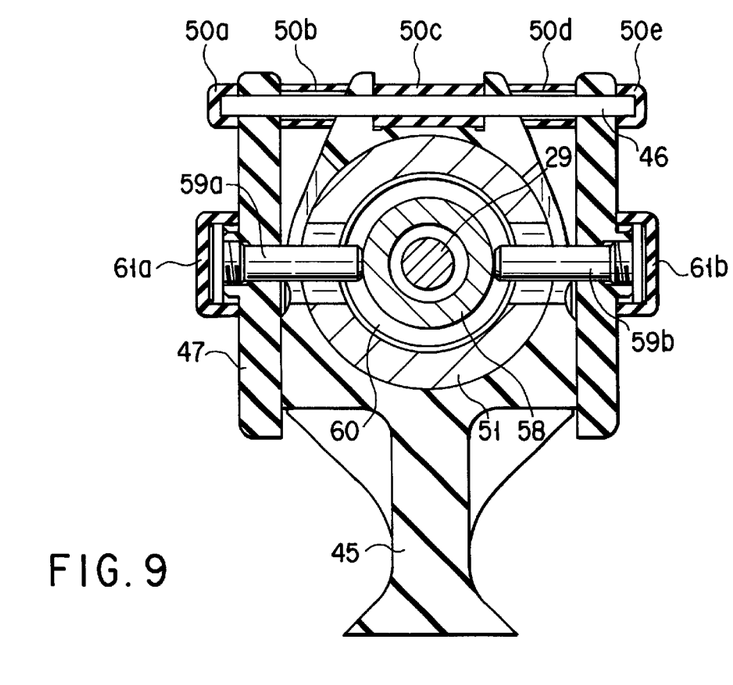
FIG. 9 is a sectional view taken along the line C—C shown in FIG. 7.

As shown in FIG. 7 and FIG. 9, pin covers 50a, 50b, 50c, 50d, and 50e each consisting of an insulation member are covered around the fulcrum pin 46. In addition, an insulation cover 51 is mounted to the fixing handle 45. A connecting member 52 having a groove engaged with the ring 9 on the ultrasonic vibrator 2 side is fixed to the proximal end side of the insulation cover 51. A connecting pin 53 serving as a high-frequency power connection connector is mounted and fixed to the proximal end of this connecting member 52 via the pin fixing member 54. A cable for supplying a high-frequency current from a high-frequency power source (not shown) is connected to the connecting pin 53. A rubber ring 55 consisting of a conductive elastomer is sandwiched between the pin fixing member 54 and the connecting member 52 in order to ensure good electrical connection. In addition, the connecting pin 53 and the pin fixing member 54 are covered with a pin cover 56 consisting of an insulation member.

An insert section fixing member 57 is turnably arranged inside of the insulation cover 51. In this case, the insert section fixing member 57 is arranged so as to sandwich a section at which the hole diameters of the insulation cover 51 and fixing handle 45 are reduced between rotating knobs 44 provided at the proximal end portion of the insert section 32. Therefore, with such configuration, when the rotating knob 44 is operated to be turned, the insert section 32 rotates at the axial direction with respect to the operating section 34.

A driving force transmitting member 58 is coupled with the proximal end of the driving shaft 41. A groove 60 engaged with driving force transmitting pins 59a and 59b provided at the movable handle 47 is provided at the center portion of the driving force transmitting member 58. The driving force transmitting pins 59a and 59b are covered with insulation caps 61a and 61b, respectively. O-rings 62 and 63 coming into close contact with the insert section fixing member 57 and the inner face of the connecting member 52 are mounted, respectively, near both ends of the driving force transmitting member 58. These O-rings 62 and 63 are made of a conductive elastomer. In addition, the inner diameter of the driving force transmitting member 54 is set to be smaller than the outer diameter of the rubber ring 64 so that the rubber ring 64 comes into close contact with the driving force transmitting member 58 over its entire periphery in its assembled state.

In the ultrasonic treatment apparatus 28 having such configuration, when the movable handle 47 is gripped, the movable handle 47 and the driving force transmitting pins 59a and 59b fixed to the movable handle 47 are turned about the fulcrum pin 46, and the driving force transmitting member 58 engaged with the driving force transmitting pins 59a and 59b are advanced or retracted in the axial direction. Therefore, the driving shaft 41 linked with the driving force transmitting member 58 is also advanced or retracted, and the jaws are turned via the fulcrum pins 39a and 39b.

In addition, the connecting pins 53 are electrically connected to the probe 29 via each of the members 54, 52, 63, 58, and 64 consisting of a conductive material. Further, in the case where the rubber ring 67 provided at the node of vibration of the probe 29 is formed by a conductive elastomer, the connecting pin 53 is electrically connected to the probe 29 even via each of the members 54, 52, 63, 58, 62, 57, 43, 36, and 67 consisting of a conductive material. Therefore, an advantageous effect similar to that of the first embodiment can be achieved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A ultrasonic treatment apparatus comprising:

a ultrasonic vibrator for generating ultrasonic vibration;

a vibration transmitting member connected to the ultrasonic vibrator at a proximal end thereof, the vibration transmitting member transmitting ultrasonic vibration generated by the ultrasonic vibrator and having a treatment section for treating tissues of a living body by the transmitted ultrasonic vibration at a tip end thereof;

a sheath removably mounted to the ultrasonic vibrator, the sheath covering the substantially entire vibration transmitting member excluding the treatment section from the outside;

a high-frequency power connection connector provided at the sheath, the connector electrically connected to a high-frequency power source via a cable for supplying a high-frequency current; and a conductive member for electrically connecting the high-frequency power connection connector to the vibration transmitting member.

2. A ultrasonic treatment apparatus according to claim 1, wherein the conductive member electrically connects the vibration transmitting member to the high-frequency power connection connector at a nodal position of ultrasonic vibration transmitted by the vibration transmitting member in order to supply a high-frequency current from the high-frequency power source to the vibration transmitting member.

3. A ultrasonic treatment apparatus according to claim 1, wherein the conductive member is provided at the vibration transmitting member.

4. A ultrasonic treatment apparatus according to claim 1, wherein the conductive member is provided at the sheath.

5. A ultrasonic treatment apparatus according to claim 1, wherein the conductive member is made of a conductive elastomer.

6. A ultrasonic treatment apparatus according to claim 1, wherein the sheath, the vibration transmitting member, and the ultrasonic vibrator can be separated with one another.

7. A ultrasonic treatment apparatus according to claim 6, wherein the conductive member is provided at the vibration transmitting member.

8. A ultrasonic treatment apparatus according to claim 6, wherein the conductive member is provided at the sheath.

* * * * *